United States Patent
Tsue et al.

(10) Patent No.: US 9,364,429 B2
(45) Date of Patent: Jun. 14, 2016

(54) ORALLY DISINTEGRATING TABLET CONTAINING HYDROXYALKYL CELLULOSE MICROPARTICLES

(71) Applicant: Nippon Soda Co., Ltd., Tokyo (JP)

(72) Inventors: Shinichiro Tsue, Joetsu (JP); Takeshi Shimotori, Joetsu (JP); Takashi Kato, Joetsu (JP)

(73) Assignee: Nippon Soda Co., Ltd., Tokyo (JP)

( * ) Notice: Subject to any disclaimer, the term of this patent is extended or adjusted under 35 U.S.C. 154(b) by 13 days.

(21) Appl. No.: 14/345,569

(22) PCT Filed: Sep. 21, 2012

(86) PCT No.: PCT/JP2012/074180
§ 371 (c)(1),
(2) Date: Mar. 18, 2014

(87) PCT Pub. No.: WO2013/047353
PCT Pub. Date: Apr. 4, 2013

(65) Prior Publication Data
US 2014/0356427 A1    Dec. 4, 2014

(30) Foreign Application Priority Data

Sep. 26, 2011  (JP) ................. 2011-209968
Jan. 30, 2012  (JP) ................. 2012-017180

(51) Int. Cl.
*A61K 9/00*   (2006.01)
*A61K 9/20*   (2006.01)
*A61K 31/167* (2006.01)

(52) U.S. Cl.
CPC ............. *A61K 9/0056* (2013.01); *A61K 9/2054* (2013.01); *A61K 31/167* (2013.01); *Y10T 428/2982* (2015.01)

(58) Field of Classification Search
CPC . A61K 9/0056; A61K 31/167; A61K 9/2054; Y10T 428/2982
See application file for complete search history.

(56) References Cited

U.S. PATENT DOCUMENTS

| 2012/0232167 A1 | 9/2012 | Takeuchi et al. |
| 2014/0034760 A1* | 2/2014 | Takeuchi et al. ................. 241/1 |

FOREIGN PATENT DOCUMENTS

| JP | 2001-322927 | 11/2001 |
| JP | 2001-342128 | 12/2001 |
| JP | 2002-207030 | 7/2002 |
| WO | 2011/065350 A1 | 6/2011 |
| WO | WO 2011/065350 | * 6/2011 |

OTHER PUBLICATIONS

International Search Report dated Dec. 11, 2012, issued in corresponding PCT Application No. PCT/JP2012/074180.
Tanimura et al., "Direct Compaction of Poorly Compactable Pharmaceutical Powders with Spray-dried HPC-L", Journal of the Society of Powder Technology, Japan, 2006, vol. 43, No. 9, pp. 648 to 652.

* cited by examiner

*Primary Examiner* — Suzanne Ziska
(74) *Attorney, Agent, or Firm* — Kenyon & Kenyon LLP

(57) ABSTRACT

An orally disintegrating tablet is obtained by dry tabletting a mixture of: hydroxyalkyl cellulose microparticles having a 50% particle size in the cumulative particle size distribution of more than or equal to 15 μm and less than 40 μm, and having a hydroxyalkyl group content of 40 to 80% by mass; a main drug as a pharmaceutical ingredient; and optionally, additives such as an excipient, a binder, a disintegrant, a lubricating agent, an agent for sustained release, a base material, a coloring agent, a pH adjusting agent, a pH buffer agent, a surfactant, a stabilizer, an acidulant, a flavoring agent, a fluidizing agent, a refreshing agent, a sweetener, a savoring component, and a sweetness intensifier.

6 Claims, 3 Drawing Sheets

ORALLY DISINTEGRATING TABLET CONTAINING HYDROXYALKYL CELLULOSE MICROPARTICLES

TECHNICAL FIELD

The present invention relates to an orally disintegrating tablet having excellent storage stability.

Priority is claimed on Japanese Patent Application No. 2011-209968, filed Sep. 26, 2011, and Japanese Patent Application No. 2012-017180, filed Jan. 30, 2012, the contents of which are incorporated herein by reference.

BACKGROUND ART

An orally disintegrating tablet that easily disintegrates in the oral cavity is a tablet which can be internally administered without water and is very useful particularly for infants or aged people with a low ability to swallow. Regarding the orally disintegrating tablets, there are available tablets which use hydroxyalkyl cellulose as an additive. For example, PTL 1 suggests an orally disintegrating tablet which contains a hydroxypropyl cellulose having, when prepared into a 20% aqueous solution, a viscosity of 2000 cps or less at 37° C., and having an equilibrium water content of 20% or less at 25° C. and a relative humidity of 75%, and which substantially does not contain any disintegrating agent. Furthermore, PTL 2 suggests an orally disintegrating tablet which contains hydroxyalkyl cellulose microparticles having a volume average particle size of greater than or equal to 0.1 μm and less than 15 μm. PTL 3 suggests a solid preparation which contains a low-substituted hydroxypropyl cellulose having a volume average particle size of 25 μm or less measured according to a dry laser diffraction method, a loose bulk density of 0.35 g/mL or more, and a tight bulk density of 0.60 g/mL or more; and sugars/sugar alcohols.

CITATION LIST

Patent Literature

[PTL 1] Japanese Unexamined Patent Application, First Publication No. 2001-342128
[PTL 2] WO 2011/065350
[PTL 3] Japanese Unexamined Patent Application, First Publication No. 2001-322927

SUMMARY OF INVENTION

Technical Problem

Conventional orally disintegrating tablets have been such that the tablets swell by absorbing moisture in air during storage, and the hardness of the tablets change over time. Furthermore, there have been restrictions in the handling during storage of the tablets, such as the occurrence of wear and tear in the tablets, as a result of a change in the hardness of the tablets over time.

Solution to Problem

That is, the present invention includes the following embodiments.

<1> An orally disintegrating tablet containing hydroxyalkyl cellulose microparticles that have a 50% particle size in the cumulative particle size distribution of more than or equal to 15 μm and less than 40 μm and have a hydroxyalkyl group content of 40 to 80% by mass.

<2> The orally disintegrating tablet described in <1>, wherein the hydroxyalkyl cellulose microparticles have a 50% particle size in the cumulative particle size of more than or equal to 15 μm and less than 25 μm.

<3> The orally disintegrating tablet described in <1> or <2>, wherein the hydroxyalkyl cellulose microparticles have a 10% particle size in the cumulative particle size distribution of 10 μm or less, and a 90% particle size in the cumulative particle size distribution of 30 μm to 60 μm.

<4> The orally disintegrating tablet described in any one of <1> to <3>, wherein the hydroxyalkyl cellulose microparticles have a viscosity of 2.0 mPa·s to 20.0 mPa·s when in the form of a 2% aqueous solution at 20° C.

<5> The orally disintegrating tablet described in <4>, wherein the hydroxyalkyl cellulose microparticles have a viscosity of 2.0 mPa·s to 2.9 mPa·s when in the form of a 2% aqueous solution at 20° C.

<6> The orally disintegrating tablet described in any one of <1> to <5>, wherein the hydroxyalkyl cellulose is hydroxypropyl cellulose.

<7> The orally disintegrating tablet described in any one of <1> to <6>, wherein the tablet is obtained by a dry formulation technique.

<8> Hydroxyalkyl cellulose microparticles having a viscosity of 2.0 mPa·s to 20.0 mPa·s when in the form of a 2% aqueous solution at 20° C., having a 50% particle size in the cumulative particle size distribution of more than or equal to 15 μm and less than 40 μm, and having a hydroxyalkyl group content of 40 to 80% by mass.

Advantageous Effects of Invention

The orally disintegrating tablet of the present invention does not easily undergo swelling caused by moisture absorption during storage, and therefore, a change in hardness over time and the resulting occurrence of wear and tear are suppressed. Accordingly, the orally disintegrating tablet of the present invention can be easily handled at the time of storage.

DESCRIPTION OF EMBODIMENTS

Figure 1:
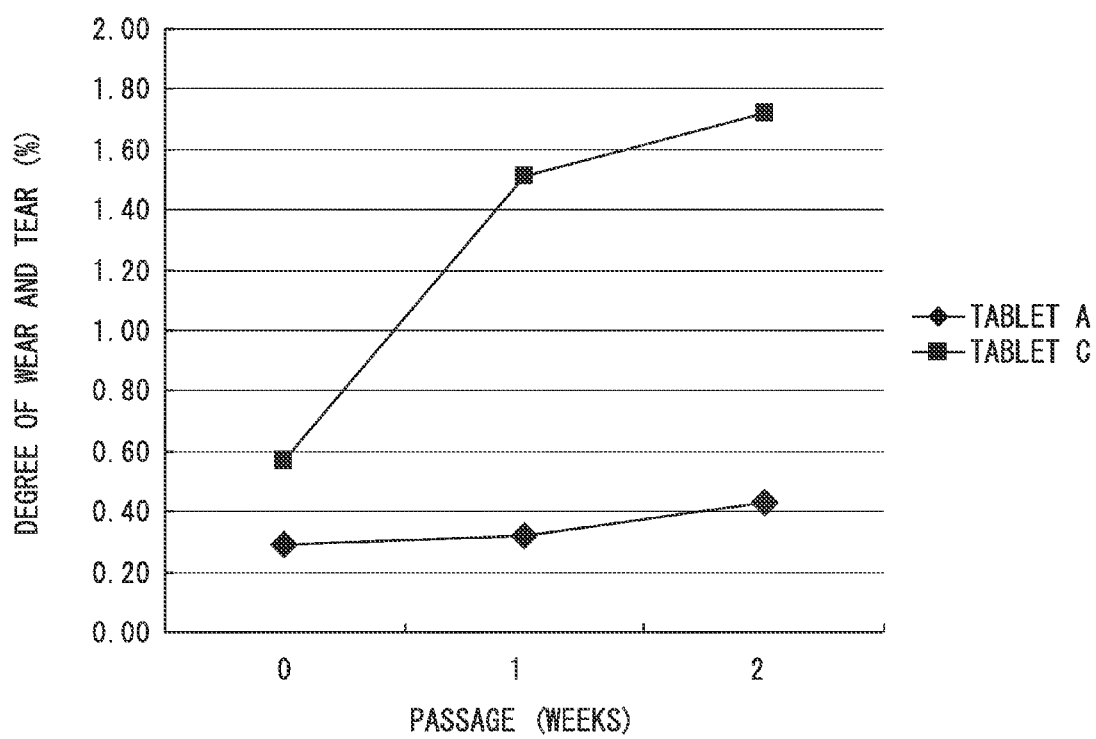
FIG. 1 is a diagram illustrating the change over time in the degree of wear and tear when tablets A and C were stored at 25° C. and a humidity of 75%.

The inventors of the present invention found that an orally disintegrating tablet produced using hydroxyalkyl cellulose microparticles having a 50% particle size in the cumulative particle size distribution of more than or equal to 15 μm and less than 40 μm and having a hydroxyalkyl group content of 40 to 80% by mass, has the change in hardness over time suppressed, and can suppress the occurrence of wear and tear that accompanies an increase in the storage time. The present invention was based on this finding, and was completed as a result of further investigations.

The orally disintegrating tablet of the present invention is formed by containing hydroxyalkyl cellulose microparticles.

The hydroxyalkyl cellulose microparticles have a 50% particle size (D50) in the cumulative particle size distribution of more than or equal to 15 μm and less than 40 μm, preferably more than or equal to 15 μm and less than 25 μm, and more preferably more than or equal to 15 μm and less than 20 μm.

Furthermore, the hydroxyalkyl cellulose microparticles used in the present invention have a 10% particle size (D10) in the cumulative particle size distribution of preferably 10 μm or less, more preferably 2 μm to 10 μm, and even more preferably 3 μm to 9 μm. Furthermore, the 90% particle size (D90) in the cumulative particle size distribution is preferably 30 μm to 60 μm, more preferably 30 μm to 50 μm, and even more preferably 30 μm to 40 μm. Furthermore, the ratio of (D90-D10)/D50 is preferably 0.1 to 7, more preferably 0.5 to 5, and even more preferably 1 to 3.

The particle size distribution of the hydroxyalkyl cellulose microparticles can be adjusted by, for example, classification, pulverization or spray drying. Preferably, hydroxyalkyl cellulose microparticles having the cumulative particle size distribution described above can be obtained by classification by an ultrasonic wave sieve, or pulverization by a jet mill.

The shape of the hydroxyalkyl cellulose microparticles used in the present invention is not particularly limited. The cumulative particle size distribution was measured using a laser diffraction type particle size distribution analyzer (for example, "LDSA-2400" manufactured by Tohnichi Computer Applications Co., Ltd.) under the conditions of an air pressure of 3.0 kgf/cm$^2$ and a focal length of 100 mm. Furthermore, the particle shape can be observed with a scanning electron microscope (for example, "JSM-7330" manufactured by JEOL, Ltd.).

The hydroxyalkyl cellulose microparticles used in the present invention can be produced according to the known method described in WO 2011/065350 or the like. Specifically, the hydroxyalkyl cellulose microparticles can be obtained by subjecting raw material cellulose to sodium hydroxide to obtain an alkali cellulose, and then subjecting the alkali cellulose and an alkylene oxide to a substitution reaction. After the end of the substitution reaction, an acid such as acetic acid or hydrochloric acid is added to the reaction liquid to neutralize sodium hydroxide, and then the reaction product can be purified. Through this substitution reaction, a part or all of —OH groups in a glucose ring unit of the cellulose are substituted with —O—(R—O)$_m$—H groups. Here, R represents a divalent alkyl group. m represents a natural number of 1 or more.

Examples of the alkylene oxide used in the substitution reaction include ethylene oxide and propylene oxide. Among these, propylene oxide is preferably used in the present invention. When the substitution reaction is carried out using propylene oxide, hydroxypropyl cellulose is obtained.

The hydroxyalkyl cellulose used in the present invention preferably has a hydroxyalkyl group content of 40 to 80% by mass, and more preferably 53 to 78% by mass. When the hydroxyalkyl group content is in this range, an orally disintegrating tablet having excellent tensile strength or excellent disintegrating properties is likely to be obtained. The hydroxyalkyl group content can be determined by the method according to USP24 (US Pharmacopoeia) or by a method according to the method described in Japanese Unexamined Patent Application, First Publication No. 2002-207030. Furthermore, the hydroxyalkyl cellulose microparticles are preferably hydroxypropyl cellulose microparticles.

The hydroxyalkyl cellulose microparticles of the present invention preferably has a viscosity of 2.0 mPa·s to 20.0 mPa·s, and more preferably 2.0 mPa·s to 2.9 mPa·s, when in the form of a 2% aqueous solution at 20° C. Viscosity is an index representing the polymerization degree of hydroxyalkyl cellulose, and is determined according to the 16$^{th}$ Revision of the Japanese Pharmacopoeia. When the viscosity is in the range described above, workability at the time of obtaining an orally disintegrating tablet becomes satisfactory. When the viscosity is higher, the tensile strength of the tablet thus obtainable tends to increase slightly. When the viscosity is lower, the disintegration time of the tablet thus obtainable tends to be shortened.

The content of the hydroxyalkyl cellulose microparticles contained in the orally disintegrating tablet of the present invention is not particularly limited, but the content is preferably 0.5 to 10% by mass, and more preferably 1 to 5% by mass, in the orally disintegrating tablet. When the relevant content is used, satisfactory orally disintegrating properties are exhibited together with excellent storage stability.

The orally disintegrating tablet of the present invention usually contains a main drug as a pharmaceutical ingredient.

Examples of the pharmaceutical ingredient include an analeptic health-promoting drug, an antipyretic analgesic antiphlogistic drug, a psychoactive drug, an anti-anxiety drug, an antidepressant drug, a sedative hypnotic drug, an antispasmodic drug, a central nervous system-acting agent, a brain metabolism improving agent, an antiepileptic agent, a sympathomimetic agent, a gastrointestinal drug, an antacid agent, an antiulcer agent, an antitussive expectorant agent, an antiemetic agent, a respiratory stimulant, a bronchodilating agent, an anti-allergic drug, a drug for dental and oral use, an antihistamine agent, a cardiotonic agent, an antiarrhythmic drug, a diuretic drug, a hypotensive drug, a vasoconstrictor drug, a vasodilator drug, a peripheral vasodilator drug, a hypolipidemic agent, a cholagogue, an antibiotic substance, a chemotherapeutic agent, an antidiabetic agent, an agent for osteoporosis, a skeletal muscle relaxant, an antidinic agent, a hormone preparation, an alkaloid-based narcotic, a sulfonamide preparation, an antipodagric drug, an anticoagulant, an antineoplastic agent, and a therapeutic drug for Alzheimer's disease. These can be used singly or in combination of two or more kinds thereof.

Examples of the analeptic health-promoting drug include vitamins such as vitamin A, vitamin D, vitamin E (d-α-tocopherol acetate or the like), vitamin B1 (dibenzoylthiamine, fursultiamin hydrochloride, or the like), vitamin B2 (riboflavin butyrate or the like), vitamin B6 (pyridoxine hydrochloride or the like), vitamin C (ascorbic acid, sodium L-ascorbate, or the like), and vitamin B12 (hydroxocobalamin acetate or the like); minerals such as calcium, magnesium or iron; proteins, amino acids, oligosaccharides, and herb medicines.

Examples of the antipyretic analgesic antiphlogistic drug include aspirin, acetaminophen, ethenzamide, ibuprofen, diphenhydramine hydrochloride, chlorpheniramine dl-maleate, dihydrocodeine phosphate, noscapine, methylephedrine hydrochloride, phenylpropanolamine hydrochloride, caffeine, anhydrous caffeine, serrapeptase, lysozyme chloride, tolfenamic acid, mefenamic acid, diclofenac sodium, flufenamic acid, salicylamide, aminopyrine, ketoprofen, indomethacin, bucolome, and pentazocine.

Examples of the psychoactive drug include chloropromazine, and reserpine. Examples of the anti-anxiety drug include alprazolam, chlordiazepoxide, and diazepam. Examples of the antidepressant drug include imipramine, maprotiline, and amphetamine. Examples of the sedative hypnotic drug include estazolam, nitrazepam, diazepam, perlapine, and phenobarbital sodium. Examples of the antispasmodic drug include scopolamine hydrobromide, diphenhydramine hydrochloride, and papaverine hydrochloride. Examples of the central nervous system acting drug include citicoline and rotilenine. Examples of the brain metabolism improving agent include vinpocetine and meclofenoxate hydrochloride. Examples of the antiepileptic agent include phenytoin and carbamazepine. Examples of the sympathomimetic agent include isoproterenol hydrochloride.

Examples of the gastrointestinal drug include stomachics and digestants such as diastase, saccharated pepsin, Scopolia extract, cellulase AP3, lipase AP, and cinnamon oil; and medicines for intestinal disorders, such as perperine hydrochloride, Lactobacilius, and Lactobacilus bifidus. Examples of the antacid agent include magnesium carbonate, sodium hydrogen carbonate, magnesium metasilicate aluminate, synthetic hydrotalcite, precipitated calcium carbonate, and magnesium oxide. Examples of the antiulcer agent include lansoprazole, omeprazole, rabeprazole, pantoprazole, famotidine, cimetidine, and ranitidine hydrochloride.

Examples of the antitussive expectorant agent include cloperastine hydrochloride, dextromethorphan hydrobromide, theophylline, potassium guaiacol sulfonate, guaifenesin, and codeine phosphate. Examples of the antiemetic include difenidol hydrochloride and metoclopramide. Examples of the respiratory stimulant include levallorphan tartrate. Examples of the bronchodilating agent include theophylline and salbutamol sulfate. Examples of the anti-allergic drug include amlexanox, and seratrodast.

Examples of the drug for dental and oral use include oxytetracycline, triamcinolone acetonide, chlorhexidine hydrochloride, and lidocaine. Examples of the antihistamine agent include diphenhydramine hydrochloride, promethazine, isothipendyl hydrochloride, and chloropheniramine dl-maleate. Examples of the cardiotonic agent include caffeine and digoxin. Examples of the antiarrhythmic drug include procainamide hydrochloride, propranolol hydrochloride, and pindolol.

Examples of the diuretic drug include isosorbide and furosemide. Examples of the hypotensive agent include delapril hydrochloride, captopril, hexamethonium bromide, hydralazine hydrochloride, labetalol hydrochloride, manidipine hydrochloride, candesartan cilexetil, methyldopa, losartan, valsartan, eprosartan, irbesartan, tasosartan, telmisartan, pomisartan, ripisartan, and forasartan.

Examples of the vasoconstrictor drug include phenylephrine hydrochloride. Examples of the vasodilator drug include carbochromen hydrochloride, molsidomine, and verapamil hydrochloride. Examples of the peripheral vasodilator drug include cinnarizine. Examples of the hypolipidemic agent include cerivastatin sodium, simvastatin, and pravastatin sodium. Examples of the cholagogue include dehydrocholic acid and trepibutone. Examples of the antibiotic substance include cephem-based antibiotic substances such as cefalexin, amoxycillin, pivmecillinam hydrochloride, cefotiam hydrochloride, cefozopran hydrochloride, cefmenoxime hydrochloride, and cefsulodin sodium; synthetic antibacterial agents such as ampicillin, ciclacillin, sulbenicillin sodium, nalidixic acid, and enoxacin; monobactam-based antibiotic substances such as carumonam sodium; and penem-based antibiotic substances and carbapenem-based antibiotic substances.

Examples of the chemotherapeutic agent include sulfamethizole hydrochloride and thiazosulfone. Examples of the antidiabetic agent include tolbutamide, voglibose, pioglitazone (hydrochloride), troglitazone, acarbose, miglitol, and emiglitate. Examples of the agent for osteoporosis include ipriflavone. Examples of the skeletal muscle relaxant include methocarbamol. Examples of the antidinic agent include meclizine hydrochloride and dimenhydrinate.

Examples of the hormone preparation include liothyronine sodium, dexamethasone sodium phosphate, prednisolone, oxendolone, and leuprorelin acetate. Examples of the alkaloid-based narcotic include opium, morphine hydrochloride, ipecacuanha, oxycodone hydrochloride, opium alkaloid hydrochloride, and cocaine hydrochloride. Examples of the sulfonamide preparation include sulfamine and sulfamethizole. Examples of the antipodagric agent include allopurinol and colchicine. Examples of the anticoagulant include dicumarol. Examples of the antineoplastic agent include 5-fluorouracil, uracil and mitomycin. Examples of the therapeutic drug for Alzheimer's disease include idebenone and vinpocetine.

The pharmaceutical ingredient may be coated in order to mask the flavor or foul odor of the ingredient, or to make the pharmaceutical ingredient suitable for enteric use or for sustained release. Examples of the coating agent include an enteric polymer, a gastric polymer, a water-soluble polymer, a sparingly soluble polymer, and a wax.

The orally disintegrating tablet of the present invention may also contain, in addition to the hydroxyalkyl cellulose microparticles, additives, such as an excipient, a binder, a disintegrant, a lubricating agent, an agent for sustained release, a base material, a coloring agent, a pH adjusting agent, a pH buffer agent, a surfactant, a stabilizer, an acidulant, a flavoring agent, a fluidizing agent, a refreshing agent, a sweetener, a savoring component, or a sweetness intensifier, as necessary.

Examples of the excipient include oligosaccharides (for example, lactose), sugars, starch, processed starch, sugar alcohols (for example, mannitol, sorbitol, xylitol, or lactitol), inorganic salts, calcium sulfate, and aluminum or magnesium silicate complexes or oxides. Examples of the excipients of inorganic salts include phosphates such as dibasic calcium phosphate dihydrate, and sulfates.

Examples of the binder include povidone, lactose, starch, processed starch, sugars, gum arabic, tragacanth gum, guar gum, pectin, wax-based binders, microcrystalline cellulose, methyl cellulose, carboxymethyl cellulose, copolyvidone, gelatin, and sodium alginate.

Examples of the disintegrant include croscarmellose sodium, crospovidone, polyvinylpyrrolidone, starch sodium glycolate, corn starch, and low-substituted hydroxypropyl cellulose.

Examples of the lubricating agent include magnesium stearate, stearic acid, palmitic acid, calcium stearate, talc, carnauba wax, hardened vegetable oils, mineral oil, polyethylene glycol, sodium stearyl fumarate, and sucrose fatty acid esters (for example, stearic acid, palmitic acid, myristic acid, oleic acid, lauric acid, behenic acid, and erucic acid).

Examples of the agent for sustained release include sodium alginate, carboxyvinyl polymers; and acrylic acid-based polymers such as an aminoalkyl methacrylate copolymer RS [EUDRAGIT RS (trade name), Rohm Pharma GmbH] and an ethyl acrylate-methyl methacrylate copolymer suspension [EUDRAGIT NE (trade name), Rohm Pharma GmbH].

Examples of the coloring agent include edible colors such as Edible Yellow No. 5, Edible Red No. 2, and Edible Blue No. 2; edible lake colors, and iron sesquioxide.

Regarding the pH adjusting agent, any pH adjusting agent that is conventionally used in the field of formulation technology can be used, and examples thereof include inorganic acids such as hydrochloric acid, sulfuric acid, hydrobromic acid, and phosphoric acid; organic acids such as acetic acid, succinic acid, fumaric acid, malic acid, oxalic acid, lactic acid, glutaric acid, salicylic acid, and tartaric acid; and salts thereof.

Examples of the pH buffer agent include amine-based buffer agents and carbonate-based buffer agents.

Examples of the surfactant include sodium lauryl sulfate, Polysorbate 80, hardened oils, and polyoxyethylene(160) polyoxypropylene(30) glycol.

Examples of the stabilizer include tocopherol, tetrasodium edetate, nicotinic acid amide, and cyclodextrins.

Examples of the acidulant include citric acid, tartaric acid, malic acid, and ascorbic acid.

Examples of the flavoring agent include various fruit flavors including strawberry flavor, and yogurt flavor, lemon oil, orange oil, and menthol.

Examples of the fluidizing agent include hard anhydrous silicic acid, hydrated silicon dioxide, and talc.

Examples of the refreshing agent include terpene-based compounds (monoterpene alcohols and the like) such as menthol, camphor, and borneol.

Examples of the sweeter include artificial and natural sweeteners, for example, sweeteners such as aspartame, acesulfame potassium, saccharin, saccharin sodium, sucralose, and sugars (for example, xylose, ribose, glucose, mannose, galactose, fructose, dextrose, sucrose, maltose, partially hydrolyzed starch (for example, syrup of maltitol), corn syrup solid, and sugar alcohols (for example, sorbitol, xylitol, mannitol, and glycerin), and combinations thereof.

Examples of the savoring component include glutamic acid, inosinic acid, and salts thereof.

Examples of the sweetness intensifier include sodium chloride, potassium chloride, organic acid salts, and phosphates.

There are no particular limitations on the method for producing an orally disintegrating tablet. Examples of the production method include a method of adding and mixing an excipient, a disintegrant and the like into a main drug, kneading hydroxyalkyl cellulose microparticles with the mixture, granulating the kneaded product in a granulating machine or the like, subsequently subjecting the granulated product to drying and particle size regulation, mixing the resultant with a lubricating agent such as magnesium stearate, and tableting this mixture (wet granule tableting method, or dry granule tableting method); and a method of mixing a main drug, an excipient, and hydroxyalkyl cellulose microparticles, mixing a lubricating agent with this mixture, and tableting the mixture (dry direct tableting method). Among these, dry formulation techniques such as a dry direct tableting method and a dry granule tableting method are preferable for the present invention.

EXAMPLES

Hereinafter, the present invention will be described in more detail by describing Examples and Comparative Examples, but these Examples and Comparative Examples are not intended to limit the scope of the present invention.

Example 1

A mixture of 3 parts by mass of hydroxypropyl cellulose microparticles (10% particle size: 6.5 µm, 50% particle size: 17 µm, 90% particle size: 35 µm, viscosity of a 2% aqueous solution at 20° C.: 2.6 mPa·s, hydroxyalkyl group content: 63% by mass), 0.5 parts by mass of magnesium stearate (lubricating agent), 2 parts by mass of crospovidone (disintegrant), 0.5 parts by mass of silica (fluidizing agent), 34.5 parts by mass of crystalline cellulose (AVICEL™ PH-102) (excipient), and 60 parts by mass of acetaminophen (bulk drug) was tableted at a tableting pressure of 10 kN using a small-sized rotary tablet machine (VELA5 0312SS2MZ, Kikusui Seisakusho, Ltd.), and thus a tablet A (tablet mass: 200 mg) was obtained. The hardness (kgf), degree of wear and tear (%) and disintegration time (min) of the tablet A measured immediately after production are shown in Table 1.

Here, the particle size distribution of the hydroxypropyl cellulose microparticles was regulated by jet mill pulverization.

The hardness (kgf) is determined by measuring the hardness of 10 tablets using an ERWEKA hardness meter (TBH28, manufactured by Erweka GmbH), and calculating an arithmetic average of the measured values.

The degree of wear and tear (%) is determined by measuring the degrees of wear and tear of 30 tablets after rotating the tablets in a wear and tear testing machine (diameter: 27 cm, TFT-1200, manufactured by Toyama Sangyo Co., Ltd.) 100 times.

The disintegration time (min) is determined by measuring, for each of six tablets, the time taken for a tablet to completely disintegrate in purified water at 37° C. according to the $15^{th}$ Revision of the Japanese Pharmacopoeia disintegration test method, and calculating an arithmetic average of the measured values.

Example 2

A mixture of 3 parts by mass of hydroxypropyl cellulose microparticles (10% particle size: 6.5 µm, 50% particle size: 17 µm, 90% particle size: 35 µm, viscosity of 2% aqueous solution at 20° C.: 2.6 mPa·s, hydroxyalkyl group content: 63% by mass), 0.5 parts by mass of magnesium stearate (lubricating agent), 2 parts by mass of crospovidone (disintegrant), 0.5 parts by mass of silica (fluidizing agent), 34.5 parts by mass of lactose/corn starch (mass ratio of 7/3) (excipient), and 60 parts by mass of acetaminophen (bulk drug) was tableted at a tableting pressure of 10 kN using the same apparatus as that used in Example 1, and a tablet B (tablet mass: 200 mg) was obtained. The hardness (kgf), degree of wear and tear (%), and disintegration time (min) of the tablet B measured immediately after production are shown in Table 1.

Here, the particle size distribution of the hydroxypropyl cellulose microparticles was regulated by jet mill pulverization.

Comparative Example 1

A mixture of 0.5 parts by mass of magnesium stearate (lubricating agent), 2 parts by mass of crospovidone (disintegrant), 0.5 parts by mass of silica (fluidizing agent), 37.5 parts by mass of crystalline cellulose (AVICEL™ PH-102) (excipient), and 60 parts by mass of acetaminophen (bulk drug) was tableted at a tableting pressure of 10 kN using the same apparatus as that used in Example 1, and thus a tablet C (tablet mass: 200 mg) was obtained. The hardness (kgf), degree of wear and tear (%), and disintegration time (min) of the tablet C measured immediately after production are shown in Table 1.

TABLE 1

|  | Example | | Comparative Example |
|---|---|---|---|
|  | 1 Tablet A | 2 Tablet B | 1 Tablet C |
| Acetaminophen [parts by mass] | 60 | 60 | 60 |
| Lactose/corn starch [parts by mass] | — | 34.5 | — |
| Avicel ™ PH102 [parts by mass] | 34.5 | — | 37.5 |
| Hydroxypropyl cellulose [parts by mass] | 3 | 3 | — |
| Silica [parts by mass] | 0.5 | 0.5 | 0.5 |
| Crospovidone [parts by mass] | 2 | 2 | 2 |
| Magnesium stearate [parts by mass] | 0.5 | 0.5 | 0.5 |
| Hardness (kgf) | 7.13 | 5.91 | 5.16 |
| Degree of wear and tear (%) | 0.29 | 0.50 | 0.57 |
| Disintegration time (min) | 0.39 | 0.57 | 0.17 |

(Stability Test)

The tablet A obtained in Example 1 and The tablet C obtained in Comparative Example 1 were stored under the conditions of 25° C. and a humidity of 75%, and the degrees of wear and tear (%) and hardness (kgf) of each of the tablets after the passage of one week and after the passage of two weeks were measured. The results are shown in FIGS. 1 and 2.

The tablet A obtained in Example 1 and the tablet C obtained in Comparative Example 1 were stored under the conditions of 40° C. and a humidity of 75%, and the degree of wear and tear (%) of each of the tablets was measured after the passage of one week and after the passage of two weeks. The results are shown in FIG. 3.

Figure 2:
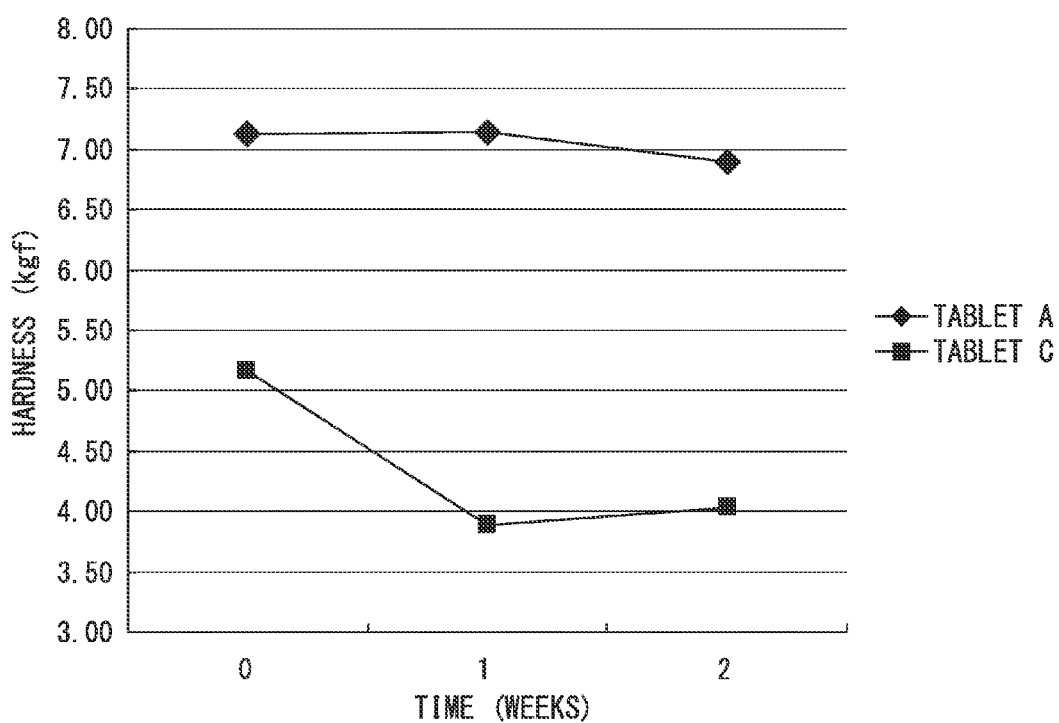
FIG. 2 is a diagram illustrating the change over time in hardness when tablets A and C were stored at 25° C. and a humidity of 75%.
Figure 3:
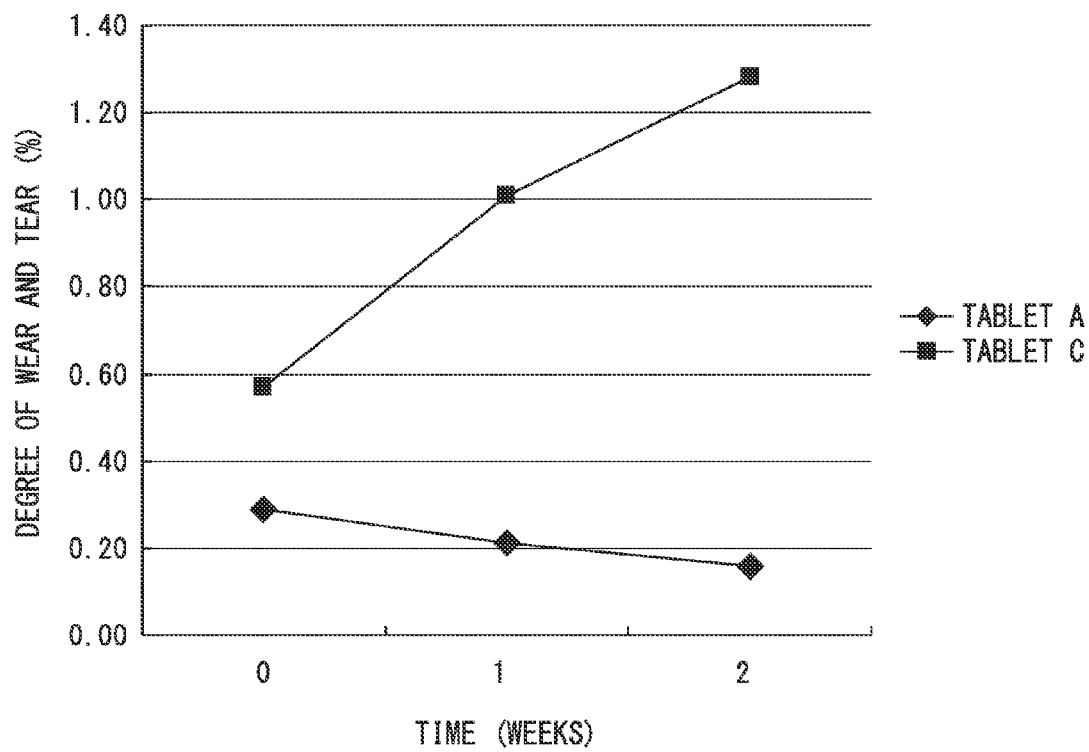
FIG. 3 is a diagram illustrating the change over time in the degree of wear and tear when tablets A and C were stored at 40° C. and a humidity of 75%.

As shown in FIGS. 1 to 3, it can be seen that the tablet A containing hydroxypropyl cellulose according to the present invention underwent a smaller change in the degree of wear and tear (%) during the storage period at 25° C. (humidity: 75%) and 40° C. (humidity: 75%), compared with the tablet C free from hydroxypropyl cellulose. Furthermore, it can be seen that the tablet A underwent a smaller change in the hardness (kgf) during the storage period at 25° C. (humidity: 75%) compared with the tablet C. That is, it can be seen that the tablet A had superior storage stability compared with the tablet C.

Example 3

A 1% aqueous dispersion (suspension) of corn starch (CORN STARCH W, manufactured by Nihon Shokuhin Kako Co., Ltd.) was heat-treated to modify the corn starch to partially pregelatinized starch, and was solubilized. Thus, a corn starch solution was obtained.

D-mannitol (MANNITE P, manufactured by Mitsubishi Shoji Foodtech Co., Ltd.) was put into a tumbling fluidized bed granulator (SPIR-A-F LOW; manufactured by Freund Corp.), and granulation was carried out while intermittently spraying the corn starch solution in the same mass amount (solid content) as that of the D-mannitol (spray pressure: 1 kg/cm$^2$, amount sprayed at the time of spraying: 17 to 20 ml/min, spraying was initiated when the temperature reached 34° C. to 35° C., and spraying was stopped when the temperature reached 28° C. to 29° C.). Thus, mannitol granules were obtained.

A mixture of 2 parts by mass of hydroxypropyl cellulose microparticles (10% particle size: 7.3 μm, 50% particle size: 25 μm, 90% particle size: 57 μm, viscosity of 2% aqueous solution at 20° C.: 2.4 mPa·s, hydroxyalkyl group content: 64% by mass; referred to as SSL-SFP), 1 part by mass of magnesium stearate (lubricating agent), 3 parts by mass of crospovidone (disintegrant), 14 parts by mass of crystalline cellulose (AVICE™ PH-102) (excipient), and 80 parts by mass of mannitol granules produced as described above, was tableted at a tableting pressure of 7 kN using a small-sized rotary tablet machine (VELA5 0312SS2MZ, manufactured by Kikusui Seisakusho, Ltd., pestle and mortar diameter: 8 mmφ lens type), and thus a tablet D1 (tablet mass: about 200 mg) was obtained. The hardness (kgf), degree of wear and tear (%) and disintegration time (min) of the tablet D1 measured immediately after production are shown in Table 2.

The particle size distribution of the hydroxypropyl cellulose microparticles was regulated by jet mill pulverization.

Example 4

A tablet D2 was obtained by the same method as that used in Example 3, except that the formulation was changed to the formulation indicated in Table 2. The hardness (kgf), degree of wear and tear (%), and disintegration time (min) of the tablet D2 measured immediately after production are shown in Table 2.

Comparative Examples 2 to 4

Tablets E1 to E3 were obtained by the same method as that used in Example 3, except that the formulation was changed to the formulations indicated in Table 2. The SL fine powder in the table is hydroxypropyl cellulose microparticles (10% particle size: 35 μm, 50% particle size: 84 μm, 90% particle size: 167 μm, viscosity of a 2% aqueous solution at 20° C.: 5.2 mPa·s, hydroxyalkyl group content: 64% by mass).

The hardness (kgf), degree of wear and tear (%) and disintegration time (min) of the tablets E1 to E3 measured immediately after production are shown in Table 2.

TABLE 2

|  | Example | | Comparative Example | | |
|---|---|---|---|---|---|
|  | 3 Tablet D1 | 4 Tablet D2 | 2 Tablet E1 | 3 Tablet E2 | 4 Tablet E3 |
| Mannitol granules (parts by mass) | 80 | 80 | 80 | 80 | 80 |
| SSL-SFP (parts by mass) | 2 | 3 | — | — | — |
| SL fine powder (parts by mass) | — | — | — | 1 | 5 |
| Avicel ™ PH102 (parts by mass) | 14 | 13 | 16 | 15 | 11 |
| Crospovidone (parts by mass) | 3 | 3 | 3 | 3 | 3 |
| Magnesium stearate (parts by mass) | 1 | 1 | 1 | 1 | 1 |
| Weight (mg) | 203.81 | 202.53 | 202.36 | 202.48 | 203.36 |
| Hardness (kgf) | 5.94 | 6.47 | 4.29 | 4.47 | 5.10 |
| Degree of wear and tear (%) | 0.38 | 0.33 | 0.45 | 0.35 | 0.35 |
| Disintegration time (min) | 0.85 | 1.11 | 0.53 | 0.42 | 0.72 |

(Stability Test)

Tablets D1, D2, and E1 to E3 were stored under the conditions of 40° C. and a humidity of 75%, and the degrees of wear and tear (%), hardness (kgf) and disintegration time (min) of each of the tablets after the passage of one week and after the passage of two weeks were measured. The results are shown in FIGS. 4 to 6.

Figure 4:
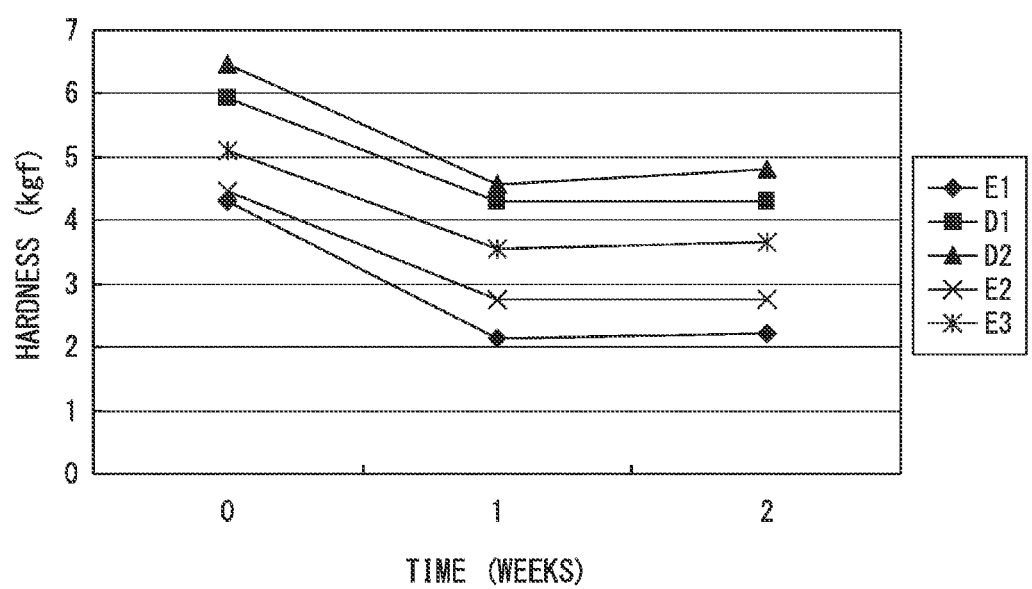
FIG. 4 is a diagram illustrating the change over time in hardness when tablets D1, D2 and E1 to E3 were stored at 40° C. and a humidity of 75%.
Figure 5:
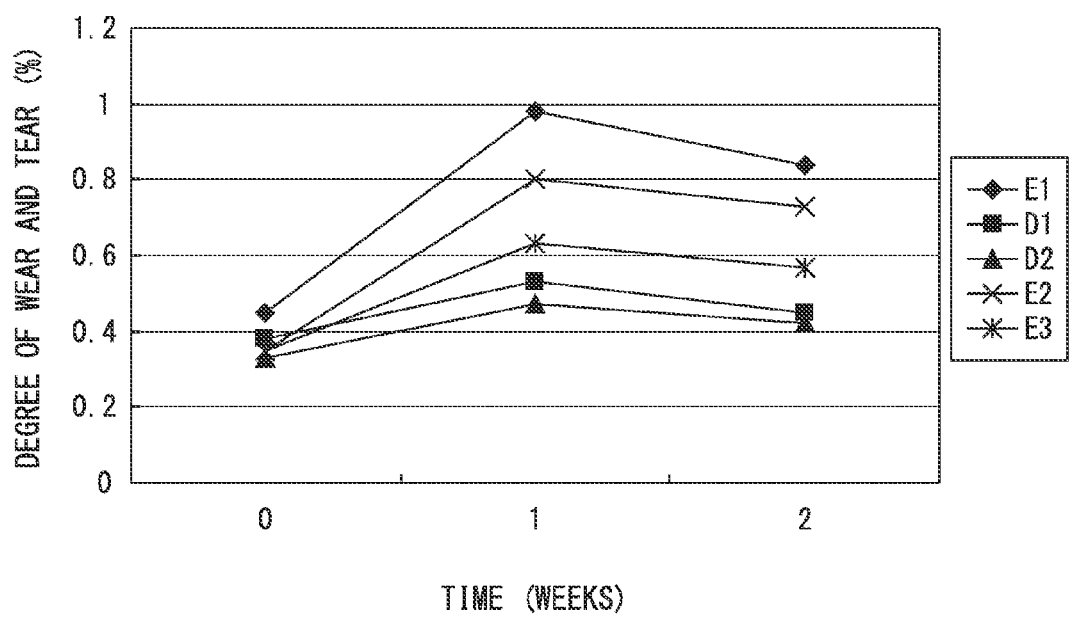
FIG. 5 is a diagram illustrating the change over time in the degree of wear and tear when tablets D1, D2 and E1 to E3 were stored at 40° C. and a humidity of 75%.
Figure 6:
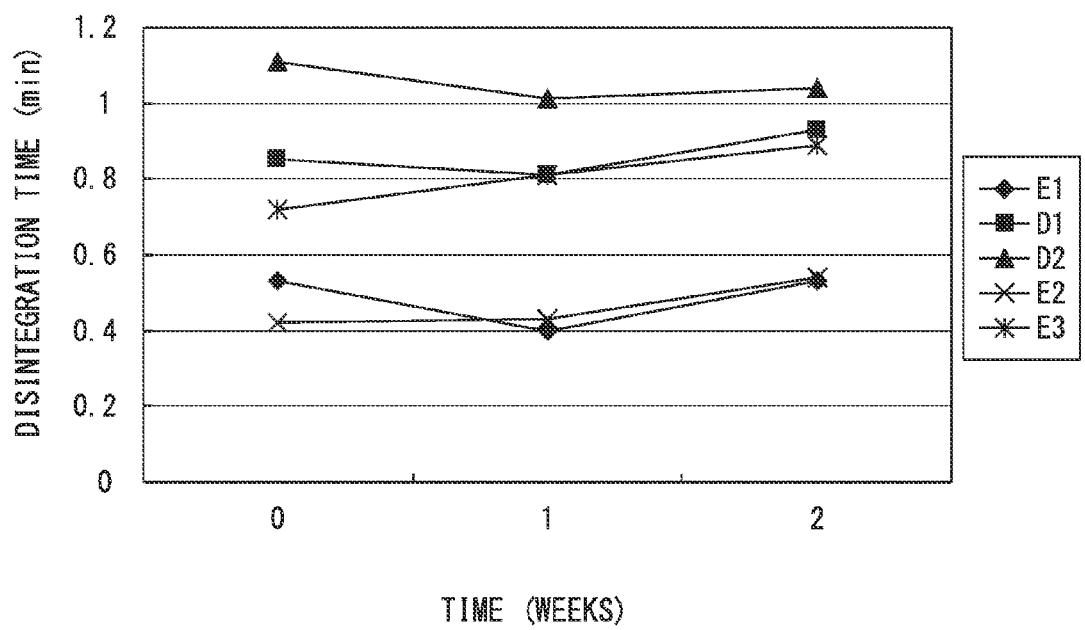
FIG. 6 is a diagram illustrating the change over time in the disintegration time when tablets D1, D2 and E1 to E3 were stored at 40° C. and a humidity of 75%.

As shown in FIGS. 4 to 6, it can be seen that the tablets containing hydroxypropyl cellulose microparticles according to the present invention (Examples 3 and 4) underwent smaller changes in the hardness, degree of wear and tear, and disintegration time under a high temperature high humidity environment, and had superior storage stability, compared with the tablets free from hydroxypropyl cellulose microparticles (Comparative Example 2) or tablets containing hydroxypropyl cellulose microparticles having a different nature (Comparative Examples 3 and 4).

INDUSTRIAL APPLICABILITY

The orally disintegrating tablet of the present invention is such that the decrease of the degree of hardness and the increase of the degree of wear and tear over time are suppressed even in a high temperature high humidity environment, and handling during storage is facilitated.

The invention claimed is:

1. An orally disintegrating tablet comprising hydroxyalkyl cellulose microparticles having a viscosity of 2.0 mPa·s to 2.9 mPa·s when in a form of a 2% aqueous solution at 20° C., a 50% particle size in a cumulative particle size distribution of more than or equal to 17 μm and less than 40 μm, and a hydroxyalkyl group content of 40 to 80% by mass.

2. The orally disintegrating tablet according to claim 1, wherein the hydroxyalkyl cellulose microparticles have a 50% particle size in the cumulative particle size distribution of more than or equal to 17 μm and less than 25 μm.

3. The orally disintegrating tablet according to claim 1 or 2, wherein the hydroxyalkyl cellulose microparticles have a 10% particle size in the cumulative particle size distribution of 10 μm or less, and have a 90% particle size in the cumulative particle size distribution of 30 μm to 60 μm.

4. The orally disintegrating tablet according to claim 1 or 2, wherein the hydroxyalkyl cellulose is hydroxypropyl cellulose.

5. The orally disintegrating tablet according to claim 1 or 2, wherein the tablet is obtained by a dry formulation technique.

6. Hydroxyalkyl cellulose microparticles having: a viscosity of 2.0 mPa·s to 2.9 mPa·s when in a form of a 2% aqueous solution at 20° C.; a 50% particle size in a cumulative particle size distribution of more than or equal to 17 μm and less than 40 μm; and a hydroxyalkyl group content of 40 to 80% by mass.

* * * * *